(12) United States Patent
Savatic et al.

(10) Patent No.: US 7,586,612 B2
(45) Date of Patent: Sep. 8, 2009

(54) PHOTOMETRIC ANALYSIS OF BIOLOGICAL SAMPLES USING IN-PLANE DETECTION

(75) Inventors: Goran Savatic, Küssnachtam Rigi (CH); Patrick Griss, Otelfingen (CH); Heinz-Michael Hein, Udligenswil (CH); Rainer Jaeggi, Thalwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 301 days.

(21) Appl. No.: 11/463,110

(22) Filed: Aug. 8, 2006

(65) Prior Publication Data

US 2007/0165229 A1    Jul. 19, 2007

(51) Int. Cl.
    *G01N 21/00* (2006.01)
(52) U.S. Cl. ...................... 356/436; 356/440
(58) Field of Classification Search ................. 356/244, 356/246, 432–440; 422/100, 102, 104; 436/164
See application file for complete search history.

(56) References Cited

U.S. PATENT DOCUMENTS 3,504,981 A * 4/1970 Malvin ........................ 356/415
3,748,044 A * 7/1973 Liston ......................... 356/409
4,279,862 A   7/1981 Bretaudiere et al.
4,325,910 A * 4/1982 Jordan ......................... 422/64
4,484,817 A * 11/1984 Nobuto et al. ............... 356/416
4,781,891 A * 11/1988 Galle et al. .................. 422/64
5,122,284 A   6/1992 Braynin et al.
5,478,750 A   12/1995 Bernstein et al.
6,476,907 B1  11/2002 Gordon

FOREIGN PATENT DOCUMENTS

WO      WO 02/43866 A3      6/2002
WO      WO 03/102559 A1    12/2003

* cited by examiner

Primary Examiner—Hoa Q Pham
(74) Attorney, Agent, or Firm—Dinsmore & Shohl LLP (57) ABSTRACT

On an analytical device for photometric analysis of chemistry and/or fluid samples comprising a rotatable disk-like body, a plurality of receptacles for fluid samples and optics for guiding light beams through the receptacles are arranged. At least part of the optics are designed and/or arranged such that at least part of the light beams is deflected and guided through the receptacles at an angle to the radially outward direction on the disk-like body which means at an angle to the radius, connecting the respective optics with the rotation axis of the disk-like body.

14 Claims, 4 Drawing Sheets

PHOTOMETRIC ANALYSIS OF BIOLOGICAL SAMPLES USING IN-PLANE DETECTION

RELATED APPLICATIONS

This application claims priority to European application EP 05017277.4 filed Aug. 9, 2005.

FIELD OF THE INVENTION

The present invention refers to an analytical device and a process for the analytical optical analysis of liquid samples.

BACKGROUND

For the optical determination of fluid chemistry or liquid samples respectively photometric analysis is commonly used and known in the art. E.g. proposed is a disk-like rotatable device on which a plurality of receptacles like cuvettes are arranged for the collection of fluid samples, the receptacles each are arranged within a photometric detection path, the respective light beam being absorbed partially for the analysis of the sample or its chemistry respectively. Photometric determination of fluid chemistry is in particular used for blood analysis, urine analysis or for any other liquid samples, where various fluid samples such as e.g. blood samples are being placed within sample cuvettes and light beams are being passed through the cuvettes, the light being partially absorbed for analysis of the blood samples.

In U.S. Pat. No. 5,122,284 a device for optically analysing biological fluids is described. On a disk a plurality of peripheral cuvettes is arranged, each of which is connected to a central connection chamber via a bifunctional path for the inlet flow of liquid into the cuvette and flow of gas out of the cuvette. A light beam oriented generally parallel to the axis of rotation is deflected once so that is passes horizontally through the fluid in the cuvette and then detected for analytical purposes. Alternatively a horizontal beam maybe once deflected vertically after passing through the fluid.

In U.S. Pat. No. 5,478,750 again photometric analysis of blood samples arranged on a rotatable disk is described, measuring the concentrations of substances like blood cell components within the liquid blood sample. The various fluid samples are arranged in cuvettes on the disk and for analytical purpose a light beam guided in perpendicular direction onto the disk surface is deflected in direction to the cuvettes within the plane of the disk.

In most known analytical devices the arrangements of the optical means and of the liquid sample containing cuvettes are arranged such that the direction of the light beam is usually in line with the radius of the rotatable disk, which means the optical deflection means or the reflective mirrors are arranged perpendicular to the radius of the rotatable disk.

Furthermore in some known devices such as described e.g. in U.S. Pat. No. 5,122,284 gas inclusions within the liquid may influence or disturb the optical analyses as liquid flow and gas removal is mixed up.

To minimize any absorption or negative influence of the material of the rotatable disk it is usually made out of a thermoplastic transparent polymer, such as e.g. poly(methyl methacrylate) (PMMA), polycarbonate, polystyrene, transparent copolyamide, etc. where so far PMMA has preferably been used. The disk-like analytical devices are usually manufactured using injection moulding technique. The optical means for the deflection of the light beam into the direction to the liquid sample containing cuvettes is achieved by providing a surface within the disk at an angle of 45° to the plane of the disk, so that the perpendicular arriving light beam is deflected without practically any absorption by the transparent polymer of the disk-like device. For producing such surfaces with a 45° angle usually respective inserts are arranged within the mould which means, that for each reflection surface a respective insert has to be arranged within the mould before the injection moulding procedure. The liquid polymer-melt is introduced into the mould at the center of the disk, which means at the rotation axis of the disk-like device, the flow of the liquid polymer is directed radially outward which may cause problems at the locations, where the inserts are arranged for the production of the reflective zone. The problem occurs due to the fact that the liquid polymer-melt is flowing around the insert, which is arranged perpendicular to the radial outward direction of the flow, so that the flow surrounds on both sides the insert for being mixed again at the backside of the insert. Practical experience showed that due to this mixing zone on the reflective surface at least partial polarisation of the light to be deflected in the direction to the cuvettes may occur, which of course is not desirable.

Furthermore the insertion of all the various inserts before the injection moulding procedure is time consuming and as a consequence the production procedure as used so far for the production of the known disk-like devices for analytical purpose is not optimal.

It is therefore one object of the present invention to optimize the production process for analytical devices as described above for photometric detection, where the surfaces of at least most of the reflective surfaces or mirror-like surfaces may guarantee optimal reflective properties, so that the deflection of the light beam is not affected by any defects within the surface.

It is a further object of the present invention to reduce the handling before and/or during the production of photometric analytical devices as described above in respect to simplify the placement of any inserts into the moulding tool establishing the mirror-like or reflective surfaces within the disk-like device for photometric analytical purpose.

It is again a further object of the present invention to reduce the influence of any gas or air inclusions within the liquid to be analytically detected which might occur due to inappropriate feeding of the receptacle with the liquid to be e.g. optically analysed.

SUMMARY OF THE INVENTION

As a consequence according the present invention proposed is an analytical device and a process for the production of an analytical device for photometric detection of biological samples comprising a rotatable disk-like body with a plurality of receptacles for a fluid sample and optical means for guiding light beams through the receptacles, wherein at least a part of the optical means are arranged such that at least a part of the light beams is first deflected and guided through the receptacles at an angle to the radially outward direction on the disk-like body which means to the radius connecting the respective optical means or the cuvette respectively with the rotation axis of the disk-like device and is secondly deflected after the passage through the receptacle out of the plane of the disk-like device.

Proposed is a device comprising a rotatable disk on which a plurality of cuvettes is arranged for collecting liquid samples to be analyzed. Furthermore reflection means are arranged within the disk-like device to direct a light beam through the cuvettes, the reflective means are arranged such that at least part of the light beam is first deflected or guided through the respective cuvette in a direction at an angle to the respective radially outward direction on the disk which means the respective radius from the disk rotation center or axis through the respective reflection means or cuvette respectively and is secondly deflected after passage through the cuvette out of the plane of the disk-like device.

According to one aspect of the present invention at least part of the optical means, primarily the means being responsible for the deflection of the arriving light beam into and through the receptacle for the liquid sample is arranged at an angle to the respective radially outward direction which is other than 90°. In other words the surface, or at least part of it, of the optical means is arranged at an angle other than 90° to the respective radius connecting the optical means with the rotation axis of the disk. As a consequence the light beam also is guided through the receptacle such as the cuvette, containing the respective liquid sample to be analyzed in a direction, which is at an angle to the radially outward direction on the disk. A further consequence is, that the entrance plane through which the light beam is entering into the receptacle or cuvette, also called detection window, is also arranged at an angle to the radially outward direction on the disk, which is other than 90°. Or defined with other words the plane of the detection window does have an angle to the radially outward direction rotation force, which is other than 90°. Finally the additional optical means to guide e.g. the light beam after detection out of the disk plane can again be arranged such that its surface is at an angle other than 90° to the radially outward direction on the rotatable disk.

According to one possible embodiment of the present invention, there are arranged a plurality of receptacles or cuvettes respectively for the collection of liquid samples such as e.g. blood, urine and the like and/or additional additives and reagents to be optically analyzed. At each receptacle at least one preceding reflective surface is arranged within the disk which is a mirror-like surface arranged at an angle of 45° to the plane of the disk for the deflection of a perpendicular arriving light beam into the plane of the disk and guiding it through the receptacle or cuvette containing the liquid sample such as e.g. blood. Of course all the mirror surfaces should be arranged such that all the light beams arriving from the same side of the disk are guided through the respective liquid sample receptacle such as the cuvette. Furthermore all the plane mirror-like surfaces, or at least part of it, are arranged at an angle to the radially outward direction on the disk which is other than 90°, so that the deflected light beam is at an angle to the radially outward direction.

In direction of the light beam after the various receptacles or cuvettes respectively again reflective surfaces or deflection mirrors can be arranged within the disk-like body such that the light beam after detection arriving from the receptacles or cuvettes respectively is deflected preferably in a perpendicular direction out of the plane of the disk-like device. Therefore this reflective surface or mirror again is at an angle of 45° to the plane of the disk, where again preferably all mirrors are arranged such that the respective light beams are guided into the same direction out of the disk plane. It can be either the same direction from which the initial light beam is guided on to the disk plane or the opposite direction out of the disk-like device.

The great advantage of arranging the optical means as proposed above is that during the injection moulding procedure for procuring the analytical disk-like device the liquid polymer-melt is not symmetrically surrounding the mirror surface or deflection plane and therefore in the middle of the surface no irregularities may occur due to the mixing of the polymer-melt. This mixing zone could either be displaced to a side area of the reflective surface where the light beam is not hitting the surface or even in case, that the surface is arranged parallel to or within a radially outward radius, the mixing zone is completely out of the surface. A further advantage of the arrangement as described above is that at the entrance window for the light beam or the detection window respectively of the receptacle no gas bubbles will accumulate within the liquid to be detected. This due the fact, that the plane is not arranged at an angle of 90° to the radially outward rotation force direction and as a consequence the gas bubbles move along the window towards an edge of the entrance plane. At the respective edge, a removal of the gas bubbles can be achieved by the arrangement of so called microchannels. As a consequence the light beam is not being affected by the undesired gas bubbles.

Furthermore according an additional aspect of the present invention it is proposed to arrange at least two separate microchannels at each receptacle or cuvette respectively—one inlet channel for feeding the receptacle with the liquid and a second channel for the removal of the gas bubbles. This in contradiction to the inlet channel as proposed within U.S. Pat. No. 5,122,284, where two flow-paths are arranged within the same channel which may lead to optical disturbances as liquid and gas bubbles may be mixed.

According to another aspect of the present invention it is proposed to arrange a circular mirror or reflection surface, which is arranged on a segment of a circle on the disk-like body of the analytical device. The cross section of the reflective surface is linear and is preferably arranged with an angle of approximately 45° to the plan of the disk. As a consequence the surface of such an optical means is not plain but rounded; which is a consequence is widening within the disk plane an arriving light beam before entering into the receptacle or cuvette. With other words only the very central portion of the arriving light beam, which again preferably arrives perpendicular to the plane of the disk is deflected within a radially outward direction of the disk, and the remaining part of the light beam is widened and as a consequence most of the light beam is in a direction at an angle to the radially outward direction of the disk. Furthermore after the cuvette, again a respective collecting optical means can be arranged, which again preferably is circular, arranged within a segment of a circle of the rotatable disk. In addition this mirror or reflective surface is designed such that the widened light beam is collected and focused e.g. onto a photodetecting means which means the widened of the first reflective surface is revoked or cancelled to a narrow light beam. But as narrowing a widened light beam to a narrow light beam is well known in the art at this place no further details should be described in respect to any further optical arrangements.

According to a further similar embodiment not only segments of the circle are covered by various circular mirror-like surfaces or reflection surfaces, but the reflection surface is covering a total circle on the optical analytical disk-like device.

The great advantage of circular optical means is, that only a very limited amount of inserts has to be placed within the mould before or during the injection moulding process for the production of the disk-like device. Of course in this case again there may occur the problem of undesired mixing zones of the liquid polymer on the side of the reflective surface, but due to the fact that the arriving light beam before entering into the receptacle is widened the problem due to uneven zones on the reflection surface is of minor importance. Furthermore, as the first optical means for deflecting the arriving light beam into direction to the receptacle are arranged near to the central axis of the disk it might be possible to provide entrance holes for the injection of the polymer-melt near to the place, where the reflection surfaces are arranged.

Further embodiments and characteristics of the present invention should be explained in more details with reference to the attached figures, in which examples are shown in more details.

DETAILED DESCRIPTION OF THE INVENTION

Figure 1:
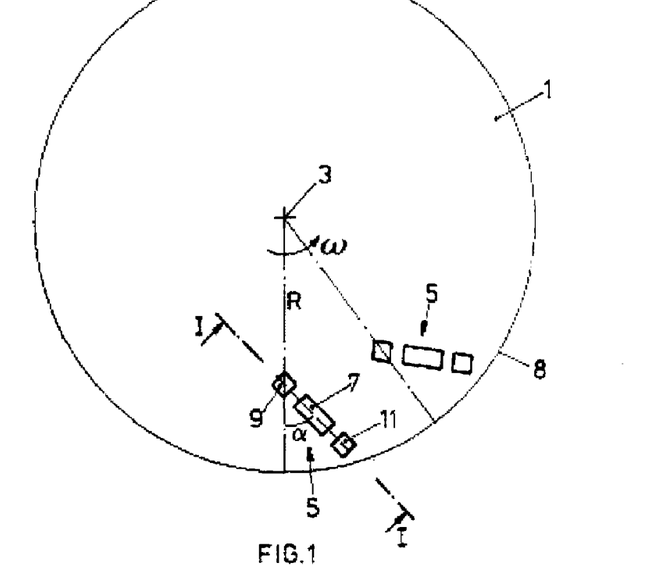
FIG. 1 shows schematically in plan view an analytical device according to the present invention showing two sections provided for photometric analysis.

FIG. 1 shows in plan view an analytical device according the present invention, comprising primarily a disk-like body 1 being rotatable around a central axis 3. In direction to the periphery 8 of the disk-like device, a plurality of sections is arranged with arrangements 5 suitable for the optical or photometric analytical detection of a liquid sample. For that purpose a plurality of receptacles or cuvettes 7 are arranged on or within the disk-like body 1. Proceeding to the receptacle or cuvette 7 arranged is a first optical means 9, in form of a plane reflective or deflective surface for the deflection of an arriving light beam into direction of the cuvette 7. After the receptacle or cuvette 7 again a second optical means 11 is arranged which again is a deflective or reflective mirror surface.

Figure 2:
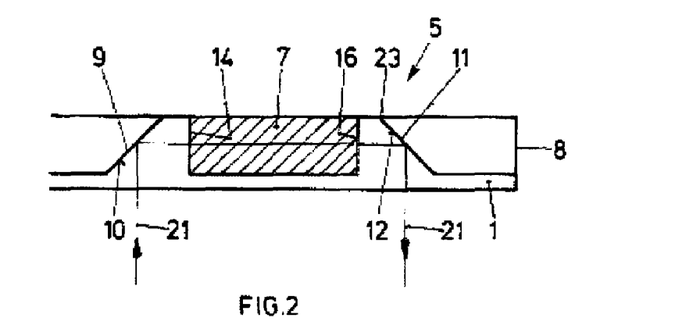
FIG. 2 shows a cross section along line I-I from FIG. 1

To better understand the particular arrangement for optical analysis, FIG. 2 shows a sectional few along line I-I from FIG. 1.

FIG. 2 shows one optical analytical arrangement 5 out of FIG. 1 in the sense of a cross sectional view through the disk-like body 1 of FIG. 1. The first optical means 9 is a deflection mirror-like surface 10, which is arranged at an angle of 45° to the plane of the disk-like body. As a result an arriving light beam 21 is deflected in direction to the cuvette 7, in which a liquid sample such as e.g. a blood sample is arranged. The light beam is entering into the cuvette 7 through an entrance plane or detection window 14 and is leaving the cuvette 7 through a second plane or window 16. After detecting the liquid, which means after being partially absorbed, the light beam is guided onto a second optical means 11 which again is represented by a deflective mirror-like surface 12 which again is arranged at an angle of 45° to the plane of the disk-like body 1.

The second optical means 11 is not absolutely necessary, as according one possible embodiment the light beam 21 after having passed the cuvette 7 can penetrate in plane of the rotatable disk-like body 1 out of the outer periphery border 8 for being detected e.g. by a photometric detection element.

The cuvette 7 preferably is an "open" cuvette for easy filling reason and may be covered by a film- or plate-like cover 23 which may be removably arranged on the disk-like body 1 after filling the various cuvettes or receptacles 7. In general the cover is arranged firmly and filling of the cuvette can be achieved through microchannels, which in general are arranged within disk-like analytical devices. The arrangement of such micro channels is well known from the art and therefore no further explanation has to be given at this point.

Figure 3:
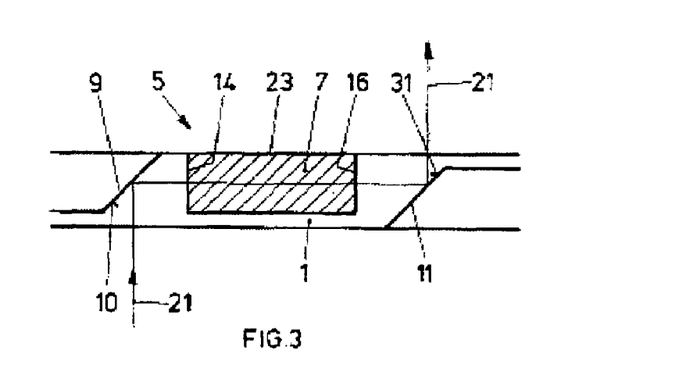
FIG. 3 shows a further possible design of the device of FIG. 1 along the I-I.

In FIG. 3 a further possible optical analytical arrangement 5 is shown along the line I-I of FIG. 1. In principal the optical arrangement is equivalent to the one shown in FIG. 2 with the exception, that the second optical means 11 is having a deflection mirror-like surface 31 guiding the light beam 21 into a direction out of the plane of the disk-like body 1, which is opposite to the direction from which initially the light beam 21 arrives into the arrangement.

As already described above, the difference of the optical arrangement compared to the state of the art is, that the optical means for deflecting the light beam is arranged such that the light beam direction through the receptacle or cuvette with the liquid sample to be detected is at an angle α to the radially outward direction, which means, the light beam is not equivalent with a radial outward direction of the disk-like body. The advantage is, that during production of the disk-like body by using injected moulding technique the liquid polymer-melt injection in the center of the disk is not surrounding the first optical means in a symmetrical way, so that the mixing zone of the polymer-melt is not in the area, where the light beam is being deflected. As a consequence no undesired effects such as e.g. polarisation of the light may occur on the reflective surface.

In case of a closed and/or completely filled receptacle or cuvette 7 the design as shown in FIG. 1 to FIG. 3 may be applied. But in case of a only partially to be filled cuvette and a cuvette filled with additional amounts of liquid, a different design could be chosen, as shown e.g. in FIG. 4.

Figure 4:
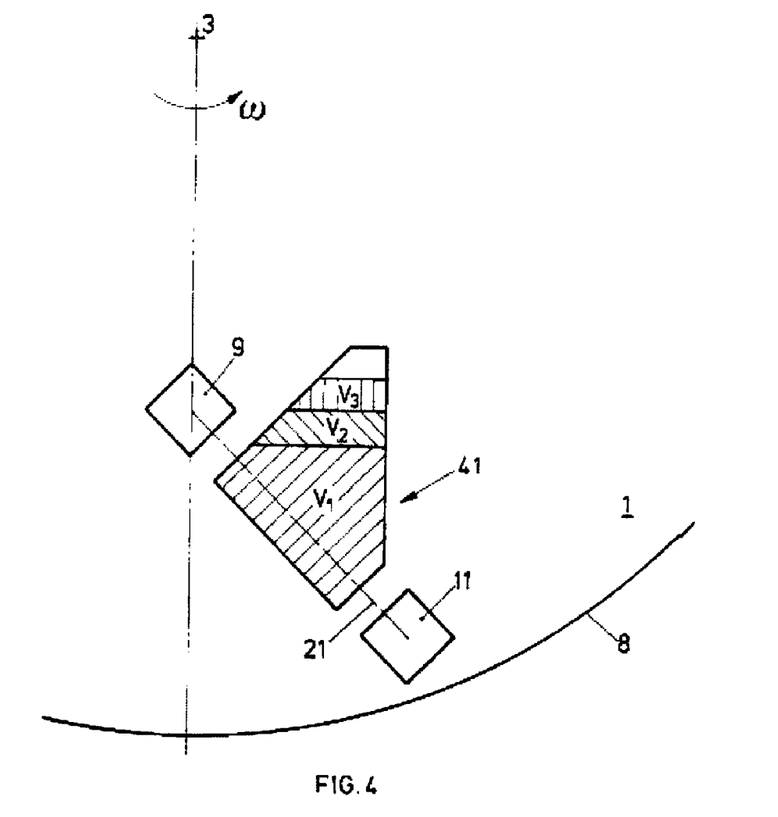
FIG. 4 shows a possible design of the receptacle or cuvette suitable for photometric analytical detection within a section as shown in FIG. 1.

Usually for an analytical purpose different liquid chemistry samples are used such as e.g. blood samples, where in a first item only the sample as such is analytically detected. In successive further items additional additive and reactants are added into the cuvette or receptacle 7. As a consequence it is important, that already in the first step or first item the light beam is guided through a "completely filled" cuvette, which means that there are no empty holes on the path of the light beam through the cuvette. Therefore according to FIG. 4 it might be necessary to use a different design of a cuvette 7 to get reliable analytical results with an arrangement as proposed according to the present invention. It is e.g. possible instead of using a rectangular cuvette 7 a cuvette design as shown in FIG. 4. The cuvette 41 as shown schematically in FIG. 4 does have an additional volume in direction to the center of the rotatable disk. In the first item a first sample covering V1 is given into the receptacle or cuvette 41, the volume is such that the light beam 21 is completely travelling through the liquid sample. After the addition of a second volume V2 e.g. through a microchannel (not shown) and appropriate mixing of the total volume again a further analysis is executed, again the light beam 21 is travelling through a totally filled volume V1 and V2 for detection purpose. In a third step a further volume V3 is added and after a further mixing process an additional analytical step by using the light beam 21 is following.

The design as shown in FIG. 4 of course only represents one possible example for the better understanding of the problem which may occur by using liquid samples with different volumes which means with different chemical steps to be analytically detected. Any other possible design can of course be used—important is, that already for the detection of the first sample volume the light beam 21 is travelling completely through the liquid sample.

Figure 5:
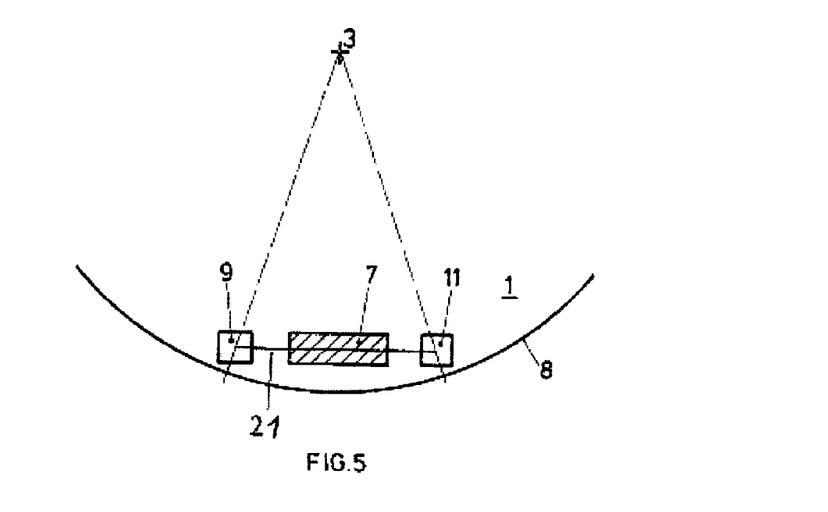
FIG. 5 shows a further possible arrangement in plan view for optical analysis suitable for a disk as shown in FIG. 1.

Furthermore it is of course possible to place the analytical arrangement in a perpendicular direction to the radially outward direction, as shown in FIG. 5.

Figure 6A:
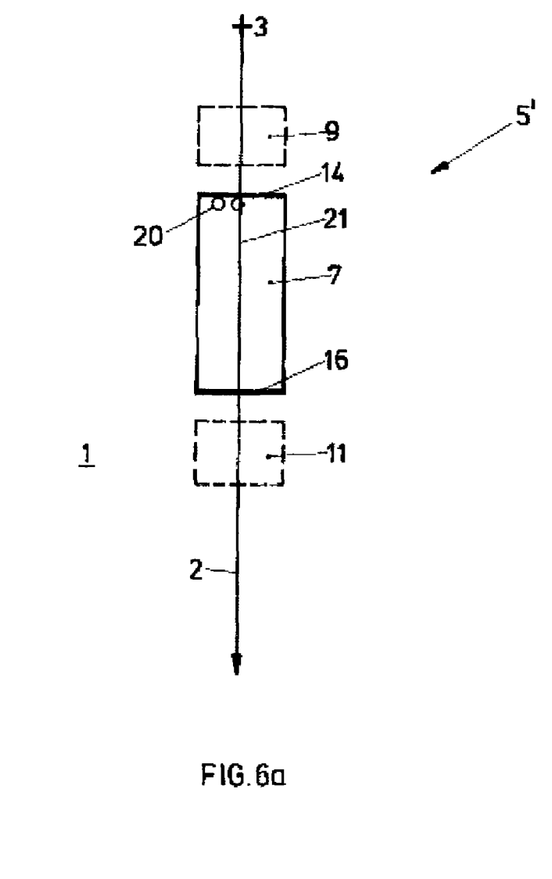
FIGS. 6a and 6b demonstrate an advantage of the arrangement as described in the present invention.
Figure 6B:
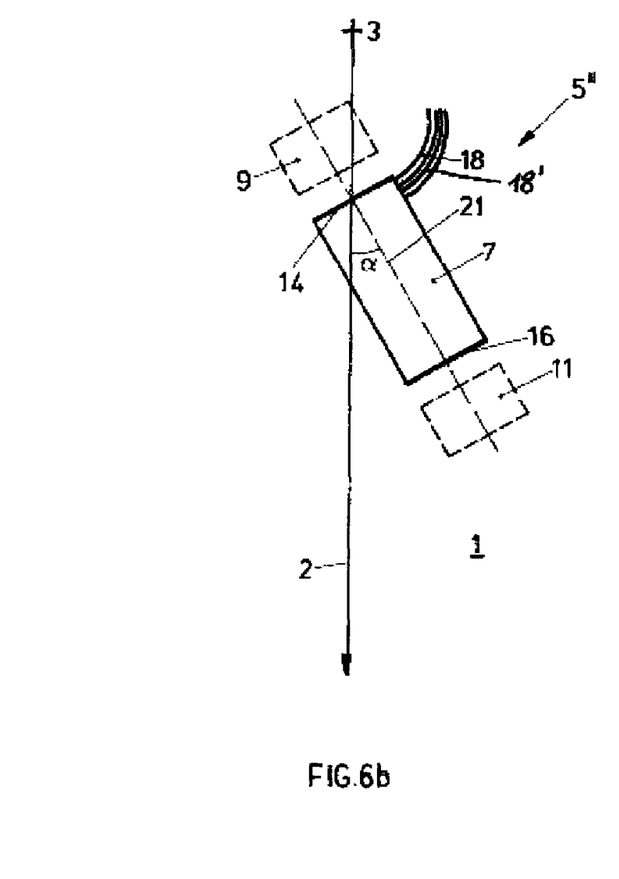

By using FIGS. 6a & 6b one great advantage of the present invention should be described in details. FIG. 6a shows an arrangement 5' as arranged on a conventional disk as known in the art. The first mirror 9, the cuvette 7 and the second mirror 11 are arranged on a line, which is in line with the radially outward direction on the rotation disk 1. With other words the light beam 21 guided through the cuvette 7 is identical with the radially outward direction 2, which also corresponds to the connection line between the first mirror 9 and the rotation axis 3 of the disk. A disadvantage of such a kind of an arrangement is, that due to the perpendicular arrangement of the entrance plane 14 or the detection mirror, through which the light beam 21 is entering into the cuvette or liquid receptacle 7, gas bubbles may accumulate mainly in the center of the window 14. Within FIG. 6a such gas bubbles are designated with the referential number 20. The forming of such gas bubbles can influence the light beam and therefore a wrong analysis result may be achieved.

Within the arrangement as shown in FIG. 6b and as designed according to the present invention, the entrance plane 14 for the entrance of the light beam 21 into the liquid receptacle 7 is at an angle to the radially outward direction, which is other than 90°. As a consequence the direction of the light beam 21 is not identical or in line with the radially outward rotation direction 2, but is including an angle α. As a consequence the gas bubbles will move towards the upper edge of the entrance window 14, where they can be evacuated through a microchannel 18. To avoid any mixing between liquid feeding and the removal of the gas bubbles it is proposed to arrange a second channel communicating with the receptacle 7—a further microchannel 18' for feeding the receptacle with the liquid to be analysed. As a consequence by using the arrangement 5'' as shown in FIG. 6b and as defined within the present invention, no forming of gas bubbles at the entrance window 14 can occur, which can influence the light beam 21. Furthermore, due the fact that microchannel 18' for feeding the receptacle with the liquid and microchannel 18 for the removal of the gas bubbles are entirely separated, it is guaranteed that there will be no mixing of inlet liquid with gas bubbles removed out of the receptacle.

Figure 7:
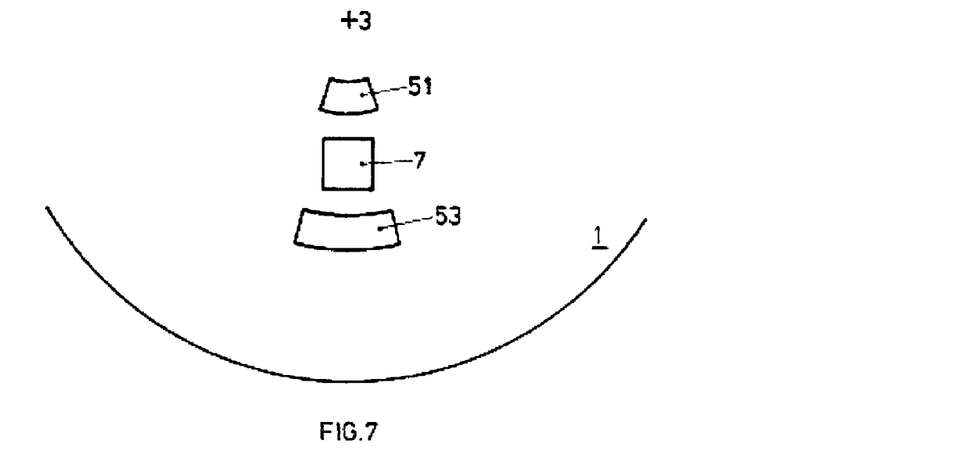
FIG. 7 shows an alternative arrangement of an optical analytical section suitable for arrangement on a disk according the present invention.

FIG. 7 shows in plan view and schematically a further possible embodiment according to the present invention. The embodiment according to FIG. 7 is showing in plane view a first mirror arrangement 51 being a circular design reflective or deflection surface representing part of a segment of a circle arranged on the disk-like body 1 of the analytical device. The mirror-like or reflection surface 51 is on one side circular and in addition does have a linear cross section, so that a light beam arriving in a perpendicular direction onto the disk plane is being deflected in direction to the cuvette or receptacle 7 containing the fluid sample. As a consequence also the succeeding reflection or mirror-like surface 53 may be designed with a circular shape and again may have a linear cross section.

Figure 8:
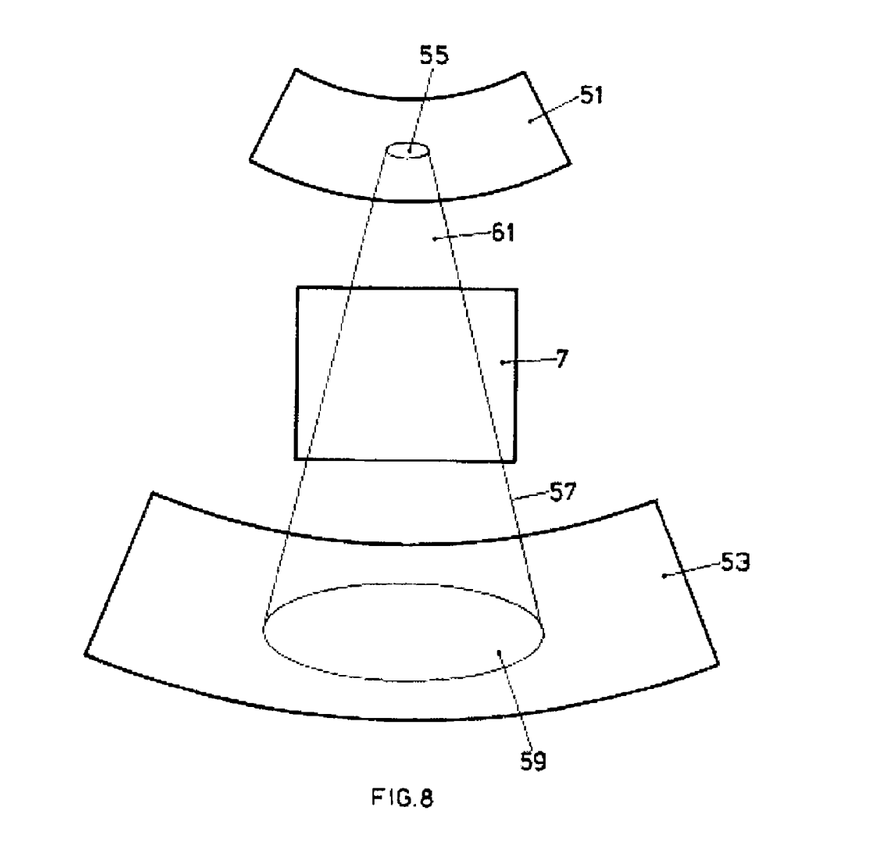
FIG. 8 shows the progression of a light beam within an optical, analytical arrangement as shown in FIG. 6.

In FIG. 8 schematically the progression of a light beam 61 is shown, which arrives in a perpendicular direction onto the plane of the disk-like body and which is deflected by the mirror-like surface 51. The light spot 55 on the first reflection surface 51 is widened within the disk plane due to the uneven circular surface of the first mirror and is proceeding as widened light beam 61 through the receptacle or cuvette 7, containing the liquid sample to be optically detected. Due to the linear cross section e.g. at an angle of approximately 45° to the plane of the disk no widening occurs perpendicular to the plane of the disk which means out of the disk plane. Finally the widened light beam 61 is collected by the succeeding second mirror-like reflection surface 53, where the light beam is arriving as widened light spot 59 For the succeeding optical detection and analysis of the light beam a further optical arrangement can be placed, in which the widened light beam again is collected to a light beam with a reduced diameter, comparable, e.g. with the entering light beam at the spot 55 on the first mirror-like surface 51. But as this is common practice in the art at this place no further explanation should be given about the succeeding optical arrangement.

As a consequence again most of the light is travelling from the spot 55 on the first mirror-like surface 51 through the receptacle or cuvette 7 in a direction, which is not equivalent with the radially outward direction of the disk-like body 1.

Of course in FIGS. 7 and 8 only one analytical arrangement is shown, while in practice spread over the whole disk-like body 1 a plurality of analytical arrangement may be placed. The great advantage of the arrangements according to FIGS. 7 and 8 is that at the production of the disk-like body and for creating the respective mirror-like reflective surface 51 and 53, only a reduced amount of inserts have to be placed within the mould for the injection moulding process. Either a total circle can be used on which the various protruding insert segments are arranged for creating the reflective surface 51 or as an alternative, an insert can be used where a circular reflective surface 51 is created which represents a complete circle and not individual segments. The same of course may happen when creating the second succeeding reflective mirror-like surface 53.

To prevent any mixing zones in the area of the reflective surface the injection holes or openings for the melted polymer could be arranged just near to the insert sections so that the mixing zones of the melt will not be in the center of the reflective surface.

The examples as shown in FIGS. 1 to 8 are of course only examples to explain the present invention in more details and do not represent any restrictions for the designs for optical analytical arrangements for the analysis of chemistry and/or liquid samples in particular in biochemical and medical analysis. Furthermore the analytical devices according the present invention and which are explained by way of examples as shown in FIGS. 1 to 8 can be used for a big variety of applications. The main application area of course covered chemistry and sample analysis in the field of bio chemistry, pharmaceutics and medicine. In particular an important application is the chemistry and the sampling of blood, urine and other liquid samples, where a great variety of analysis possibilities are possible. Usually not only blood or urine as such is used, but also in combination with a great variety of additives and reactants. Furthermore using the rotation of the disk-like device e.g. blood or urine can be analyzed at various steps of separation between e.g. plasma and blood cells. Of course in general any kind of sampling analysis is possible and the use of rotatable disk-like devices in principal is well known in the art.

Further more the optical analytical process as such is also known from the art which means the process using the device according to the present invention may include any kind of light beam wave lengths which are commonly used in analytical processes. For instance any kind of laser beams or commonly used light in the range e.g. from 300 to 800 nm etc. can be applied. Also the material used for the production of a disk-like device is known and preferably a transparent polymer is used such as e.g. PMMA. But of course also all kind of suitable transparent polymers maybe used like e.g. polycarbonate, transparent polystyrene, transparent polyamides, etc.

What is claimed is:

1. An analytical device for photometric analysis of a biological sample, the device comprising a rotatable disk-like body with a receptacle for the biological sample and optical means for guiding a light beam through the receptacle, wherein the optical means is arranged such that the light beams is firstly deflected and guided through the receptacle at an angle to the radially outward direction on the disk-like body and is secondly deflected after the passage through the receptacle out of the plane of the disk-like device, wherein the receptacle comprises a first microchannel for inlet of the sample to be analyzed into the receptacle and a second microchannel for removal of gas bubble that accumulate within the receptacle, said second microchannel being entirely separate from the first microchannel to avoid mixing of inlet liquid with gas bubble removed out of the receptacle.

2. The device of claim 1 wherein the optical means comprises an even reflective surface and is arranged at an angle other than 90° to the radially outward direction on the disk-like body.

3. The device of claim 1 wherein the optical means comprises at least a first reflective surface positioned prior to the receptacle and a second surface positioned following the receptacle.

4. The device of claim 3 wherein the reflective surfaces of the optical means are arranged at an angle of approximately 45° to the plane of the disk-like device such that a perpendicular arriving light beam onto the plane of the disk is deflected into the plane of the disk-like device towards the respective receptacle arranged on or within the disk-like body.

5. The device of claim 1 wherein a detection window comprising an entrance plane for entrance of the light beam into the receptacle is arranged at an angle to the radially outward direction on the disk, the angle being other than 90°.

6. The device of claim 1 wherein succeeding the receptacle a further optical means is arranged for deflecting the light beam after passage through the receptacle out of the plane of the disk-like body.

7. The device of claim 6 wherein the further optical means comprises an even reflective surface arranged at an angle of approximately 45° to the plane of the disk-like device such that the light beam after passage through the receptacle is deflected out of the plane of the disk-like body in a perpendicular direction to the disk plane.

8. The analytical device of claim 1 wherein the receptacle comprises a volume design extending towards the center of the disk-like body such that the light beam passage through the receptacle completely through liquid volume is guaranteed already when the volume of the receptacle is only partially filled with liquid sample.

9. The device of claim 8 wherein succeeding the receptacle a further optical means is arranged comprising a reflective surface of a circular shape, the surface having a linear cross-sectional shape.

10. The device of claim 1 wherein the optical means comprises a reflective surface with a circular shape such that the reflective surface is arranged on a circle of the rotatable disk-like device.

11. The device of claim 10 wherein a cross section of the reflective surface is linear and is at an angle of approximately 45° so that a light beam arriving perpendicular to the plane of the disk is deflected onto the plane of the disk-like body and at the same time is widened within the disk plane to be passed through the receptacle.

12. A process for the production of an analytical device of claim 1 comprising the step of injecting a polymer-melt into a mould, wherein for arranging the optical means respective inserts are arranged within the mould before the injection of the melt such that at least part of the surface of the optical means provided to create the reflective surface for a light beam is arranged at an angle to the radially outward direction on the disk-liked body and at least part of the surface of the reflective surface is circular and is arranged on a circle of the disk-like body to be produced by injection moulding.

13. An analytical process for photometric analysis of a fluid biological sample arranged on a rotatable disk-like body with a receptacle for the fluid sample, comprising providing the fluid sample to the receptacle through a first microchannel of the disk-like body, guiding a light beam by optical means arranged on the disk-like body through the receptacle in a direction which is at an angle to the radially outward direction of the rotatable disk-like body or the radially outward directed rotation force respectively, deflecting the light beam after passage through the receptacle out of the plane of the disk-like body, using the partial absorption of the light beam guided through the receptacle for analytical purpose, and removing gas bubbles accumulated within the receptacle by a second microchannel of the disk-like body that is entirely separate from the first microchannel to avoid mixing of the fluid sample with the gas bubbles removed out of the receptacle.

14. The process of claim 13 wherein in a first step, a first volume is within the receptacle being detected by the light beam which is guided through the receptacle and which light beam is being photometrically detected for analytical purpose; in a second step an additional volume is added into the receptacle and after mixing a second optical analytical step is executed, and if necessary further steps are following by adding an additional amount of liquid sample volume into the receptacle and after mixing a further optical or photometric analytical step is being added.

* * * * *

UNITED STATES PATENT AND TRADEMARK OFFICE
CERTIFICATE OF CORRECTION

| | |
|---|---|
| PATENT NO. | : 7,586,612 B2 |
| APPLICATION NO. | : 11/463110 |
| DATED | : September 8, 2009 |
| INVENTOR(S) | : Goran Savatic et al. |

Page 1 of 1

It is certified that error appears in the above-identified patent and that said Letters Patent is hereby corrected as shown below:

Col. 9, line 17, "removal of gas bubble" should read -- removal of gas bubbles --

Col. 9, line 21, "with gas bubble" should read -- with gas bubbles --

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,586,612 B2  Page 1 of 1
APPLICATION NO. : 11/463110
DATED : September 8, 2009
INVENTOR(S) : Savatic et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 332 days.

Signed and Sealed this

Twenty-first Day of September, 2010

David J. Kappos
*Director of the United States Patent and Trademark Office*